United States Patent [19] [11] Patent Number: 4,945,899

Sugiyama et al. [45] Date of Patent: Aug. 7, 1990

[54] METHOD OF AND APPARATUS FOR ARTIFICIAL RESPIRATION IN SYNCHRONISM WITH VOLUNTARY BREATHING OF A PATIENT

[75] Inventors: Yoshihiko Sugiyama, Tokyo; Muneshige Kurahashi, Tokorozawa; Sakari Yokoyama, Narashino; Tadayuki Ishihara, Tokyo, all of Japan

[73] Assignee: Nihon Kohden Corporation, Tokyo, Japan

[21] Appl. No.: 219,075

[22] Filed: Jul. 14, 1988

[51] Int. Cl.$^5$ ............................................. A61H 31/00
[52] U.S. Cl. ...................................... 128/28; 128/30; 128/721; 128/777
[58] Field of Search .................. 128/28, 30, 777, 721, 128/204.21, 204.23, 204.26, 202.12

[56] References Cited

U.S. PATENT DOCUMENTS

| | | | |
|---|---|---|---|
| 3,942,513 | 3/1976 | Frank | 128/28 |
| 3,951,143 | 4/1976 | Kitrilakis et al. | 128/204.23 |
| 3,976,064 | 8/1976 | Wood et al. | 128/204.21 |
| 4,141,356 | 2/1979 | Smargiassi | 128/204.26 X |
| 4,303,077 | 12/1981 | Lewin et al. | 128/777 |
| 4,340,045 | 7/1982 | Manley | 128/204.26 |
| 4,414,982 | 11/1983 | Durkan | 128/204.26 |
| 4,495,952 | 1/1985 | Klett | 128/777 |
| 4,539,984 | 9/1985 | Kiszel et al. | 128/204.23 |
| 4,597,394 | 7/1986 | Sackner | 128/777 |
| 4,657,026 | 4/1987 | Tagg | 128/721 |
| 4,744,356 | 5/1988 | Greenwood | 128/204.26 |

FOREIGN PATENT DOCUMENTS 176348 8/1986 Japan .

OTHER PUBLICATIONS

"Clinical Applications of BodyVentilators", by Nicholas S. Hill, published in Chest, The Pulmonary Journal, on pp. 897–905 in vol. 90, Jul.–Dec., 1986 of Official Publication of the American College of Chest Physicians.

Primary Examiner—Randall L. Green
Assistant Examiner—Stephanie L. Iantorno
Attorney, Agent, or Firm—Hoffmann & Baron

[57] ABSTRACT

A method of and apparatus for effecting artificial respiration in synchronism with a patient's voluntary breathing. The apparatus is in the form of an external body ventilator with an assistor, and comprises a jacket, a suction pump, a suction pipe, a changeover device, a jaw movement detection device, and a changeover controlling device. The jacket has a rigid shell for surrounding the chest of a patient and forming an air-tight chamber between the chest and the rigid shell when the jacket is applied to the chest of the patient. The suction pipe is in fluid communication with the air-tight chamber of the jacket, and the changeover device is for effecting a changeover between releasing the air in the air-tight chamber through the suction pipe and into the atmosphere during voluntary respiration, and connecting the suction pipe to the suction pump during artificial respiration. The jaw movement detection device produces a signal corresponding to the movement of the jaw of the patient, and the changeover control device determines a timing of voluntary breathing by the patient on the basis of a signal detected by the jaw movement detection device, and controls the changeover device on the basis of the timing.

1 Claim, 2 Drawing Sheets

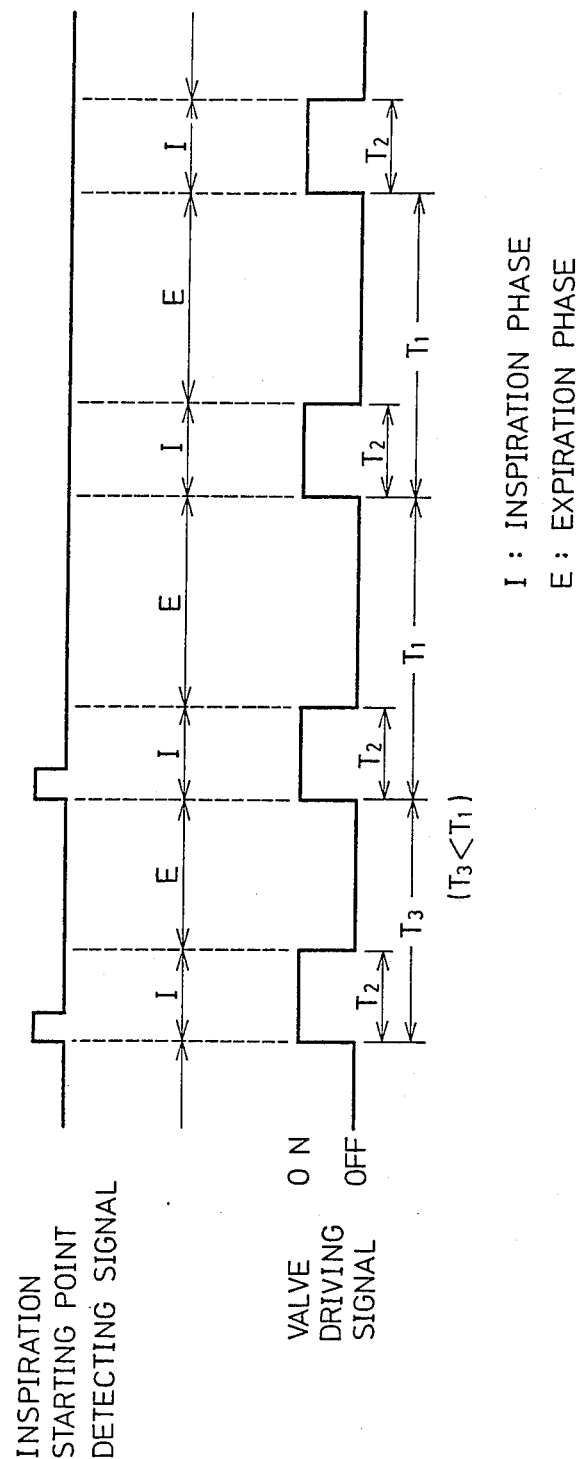

METHOD OF AND APPARATUS FOR ARTIFICIAL RESPIRATION IN SYNCHRONISM WITH VOLUNTARY BREATHING OF A PATIENT

BACKGROUND OF THE INVENTION

1. Field of the Invention

The present invention relates to an external body ventilator of the assistor-controller type, and more particularly relates to improved mechanisms for controlling the timing of artificial respiration in synchronism with the voluntary breathing movement of a patient connected to an external body ventilator.

2. Setting for the Invention

Although there are various types of artificial respiration devices, one popular device used by many is a positive-pressure type device which applies positive-pressure directly to the trachea. Using this device, it is possible to effect artificial respiration positively, i.e. by the direct introduction of air into and drawing of air from the lungs. However, with such a device, a tracheotomy is required. Naturally, this surgical procedure requires that the dissected portion of the trachea be disinfected in order to prevent infection, and in addition, there are several other drawbacks as well. In particular, the patient connected to such a device and having undergone such a surgical procedure is unable to consume solid food or engage in conversation with others.

Other prior art respiratory devices include external body ventilators, one of which is most commonly known as the "iron lung". The iron lung, however, is very large in scale and its efficiency is quite poor. Consequently, it has been used only rarely in recent years. Notably, the iron lung is a negative-pressure type device which effects inhalation and expiration of respiratory gases by way of providing an air-tight contained negative atmospheric pressure environment about a patient's chest, to cause the inflow and outflow of respiratory gases from the patient's respiratory system.

Another negative-pressure type device is the Cuirass ventilator which uses a jacket having a rigid shell that surrounds the chest portion of a patient. The jacket, when applied to the patient, is adapted to form an air-tight chamber between the patient's chest portion and the rigid shell. By reducing the air-tight chamber to a negative atmospheric pressure, artificial respiration is performed. In recent years, the advantages of this type of device have come to be recognized, since it does not require a tracheotomy of the patient, and also because it can be operated quite simply.

Among such external body ventilators, there is one in particular which employs an assistor-controller, as disclosed in Japanese Patent Laid open Application No. 176348/1986. According to this assistor-controller, when the patient is breathing voluntarily, artificial respiration can be performed in synchronism with the timing of a patient's voluntary breathing, and, when the patient ceases to breathe voluntarily, artificial respiration can be performed at a predetermined timing.

In the assistor-controller disclosed in Japanese Patent Laid open Application No. 176348/1986, the airway pressure, flow rate of respiration, the temperature of the nasal cavity of the patient, etc., have conventionally been used as biophysiological signals for purposes of detecting the timing of a patient's voluntary breathing. Using biophysiological signals of such quantitative parameters, the assistor-controller can be operated in synchronism with a patient's voluntary breathing.

However, such prior art methods and apparatus employing conventionally detected biophysiological signals described above are plagued with several significant shortcomings and drawbacks when the timing of voluntary breathing is determined on the basis of such signals. For example, in the case of a patient whose breathing movement is weak, as when a patient is suffering from myodystrophia, the signal to noise (S/N) ratio of conventionally detected biophysiological signals becomes extremely poor, possibly resulting in a malfunctioning of the apparatus.

Another principal drawback accompanying the use of conventional biophysiological signals is that such detective signals do not directly indicate the voluntary breathing movement of a patient, but rather are generated indirectly as a result of breathing. Thus, such biophysiological signals incur some time lag after the breathing movement and thus provide a source of error in efforts to synchronize the assistor-controller apparatus with the voluntary breathing movement of a patient.

In addition, conventionally detected biophysiological signals described above require that the sensors be installed on the patient. Consequently, it is often technically difficult to install on a patient a pressure sensor in the case of airway pressure detection, a flow rate sensor in the case of flow rate of respiration detection, and a temperature sensor in the case of nasal cavity temperature detection. Moreover, prior art biophysiological signal detection methods and apparatus are in general unpleasant to wear, and pose great discomfort to the patient as well.

Most significantly, however, using prior art biophysiological signal detection methods and apparatus, it is difficult to accurately synchronize the operation of artificial respiratory apparatus with a patient's voluntary breathing. Most importantly, prior art methods and apparatus have not provided an effective way of achieving such objectives in an accurate and also in a comfortable manner from the patient's viewpoint.

Accordingly, a primary object of the present invention is to provide a method of effecting artificial respiration and synchronism with a patient's voluntary breathing, utilizing principles of jaw movement detection, thereby overcoming the above-described shortcomings and drawbacks of prior art methodologies.

A further object of the present invention is to provide such a method while employing a negative-pressure generation means capable of effecting synchronus artificial respiration when the patient is breathing voluntarily, and effecting artificial respiration at a predetermined rate when the patient has stopped voluntary breathing.

An even further object of the present invention is to provide such a method utilizing an acceleration pick up installed on the jaw of a patient, for producing a signal corresponding to the change in velocity of the patient's jaw during breathing movements. Such signal detection is used for determining a timing corresponding to the voluntary breathing of the patient.

A further object of the present invention is to provide apparatus for effecting artificial respiration in synchronism with voluntary breathing of a patient, utilizing jaw movement detection.

Other and further objects of the present invention will be explained hereinafter, and will be more particularly delineated in the appended claims, and other objects of the present invention will hereinafter become apparent to one with ordinary skill in the art to which the present invention pertains.

SUMMARY OF THE INVENTION

The apparatus of the present invention can be of the form of an external body ventilator comprising a jacket, a suction pipe, a changeover means, a jaw movement detection means and a changeover controlling means. The jacket has a rigid shell for surrounding the chest of a patient and forms an air-tight chamber between the chest and the rigid shell when the jacket is applied to the chest of the patient. The suction pipe is connected so that it is in fluid communication with the air-tight chamber of the jacket, and the changeover means is for effecting a changeover between releasing the air in the air-tight chamber through the suction pipe into the atmosphere during exhalation, and connecting the suction pipe to the suction pump during inhalation. The jaw movement detection means produces a signal corresponding to the movement of the patient's jaw, and the changeover controlling means determines a timing of voluntary breathing by the patient, on the basis of the signal detected by the jaw movement detection means. On the basis of the determined timing, the changeover means is controlled by the changeover controlling means.

In the preferred embodiment, the changeover controlling means controls the changeover means at a predetermined timing when the determined timing exceeds a predetermined time interval.

In the preferred embodiment, the jaw movement detection means is an acceleration pick-up which is installed on the jaw of a patient, and detects a change in the velocity of the jaw during the patient's breathing movements. Alternatively, however, the jaw detection means can be a displacement sensor for detecting an amount of displacement between the jaw and the patient's throat over a predetermined time interval.

Another aspect of the present invention involves a method of effecting artificial respiration in accurate synchronism with a patient's voluntary breathing. The method comprises providing about a patient's chest, an air-tight contained atmosphere (e.g. an air-tight pressure chamber), controllable between atmospheric pressure and a predetermined negative pressure, using an atmospheric-to-negative pressure generation means including a suction means. The atmospheric-to-negative pressure generation means is capable of effecting artificial respiration in synchronism with voluntary patient breathing when the patient is breathing voluntarily, and effecting artificial respiration at a predetermined timing when the patient has stopped voluntary breathing. A jaw movement detection means is provided on the patient's jaw for determining the movement of the jaw and for producing a signal corresponding to the jaw movement. On the basis of the signal determined above, a timing is determined for voluntary breathing of the patient, and the atmospheric-to-negative pressure generation means is controlled in order to effect on the basis of the determined timing, synchronous artificial respiration of the patient when the patient is determined to be voluntarily breathing, and to effect artificial respiration at a predetermined timing when the patient is determined to have stopped voluntary breathing.

In the preferred embodiment, the atmospheric-to-negative pressure generation means comprises apparatus of the present invention, but may comprise alternative apparatus utilizing jaw movement detection for generating signals representative of jaw movement, from which a timing for voluntary breathing of the patient can be determined in accordance with the principles of the present invention.

In the preferred embodiment of the method of the present invention, provision of the jaw movement detection means comprises installing an acceleration pick-up on the jaw of the patient, and producing a signal corresponding to the change in the velocity of the jaw. In the alternative embodiment, the provision of the jaw movement detection means comprises installing a displacement sensor on the jaw of the patient and producing a signal corresponding to the amount of displacement between two points extending from the jaw to the throat of the patient.

As a result of the present invention, a patient wearing artificial respiratory apparatus, such as a external body ventilator utilizing an assistor-controller, can receive artificial respiration in synchronism with his or her voluntary breathing, while using a comfortable jaw movement sensor which avoids the shortcomings and drawbacks of prior art methods and apparatus.

In developing the present invention, applicants have discovered that a patient suffering from myodystrophia, often compensates for decreased ventilation volume capacity resulting from weakened breathing muscles by performing exaggerated jaw movement while breathing. In particular, a patient's jaw moves upwardly during inspiration (i.e. inhalation), and moves downwardly during expiration (i.e. exhalation).

Accordingly, the external body ventilator of the present invention is provided with the capacity of detecting jaw movement which is interlinked with breathing movement, and producing corresponding thereto for use in the assistor-controller of the external body ventilator.

Since the timing of the patient's voluntary breathing is detected from the movement of his or her jaw, artificial respiration (i.e. breathing) performed by the assistor of the present invention is very accurately synchronized with the voluntary breathing of the patient, and without the accompanying time delay characteristic of prior art devices.

While the present invention is particularly effective for patients suffering from paralysis as a result of neuromuscular disorders as in the case of myodystrophia, it also has been found to be effective for patients suffering from other physical disorders as well.

BRIEF DESCRIPTION OF THE DRAWINGS

For a further understanding of the objects of the present invention, reference is made to the following detailed description of the preferred embodiment which is to be taken in connection with the accompanying drawings, wherein:

FIG. 2 is a timing chart used in describing the operation of the external body ventilator of FIG. 1.

DETAILED DESCRIPTION OF THE PREFERRED EMBODIMENT

Figure 1:
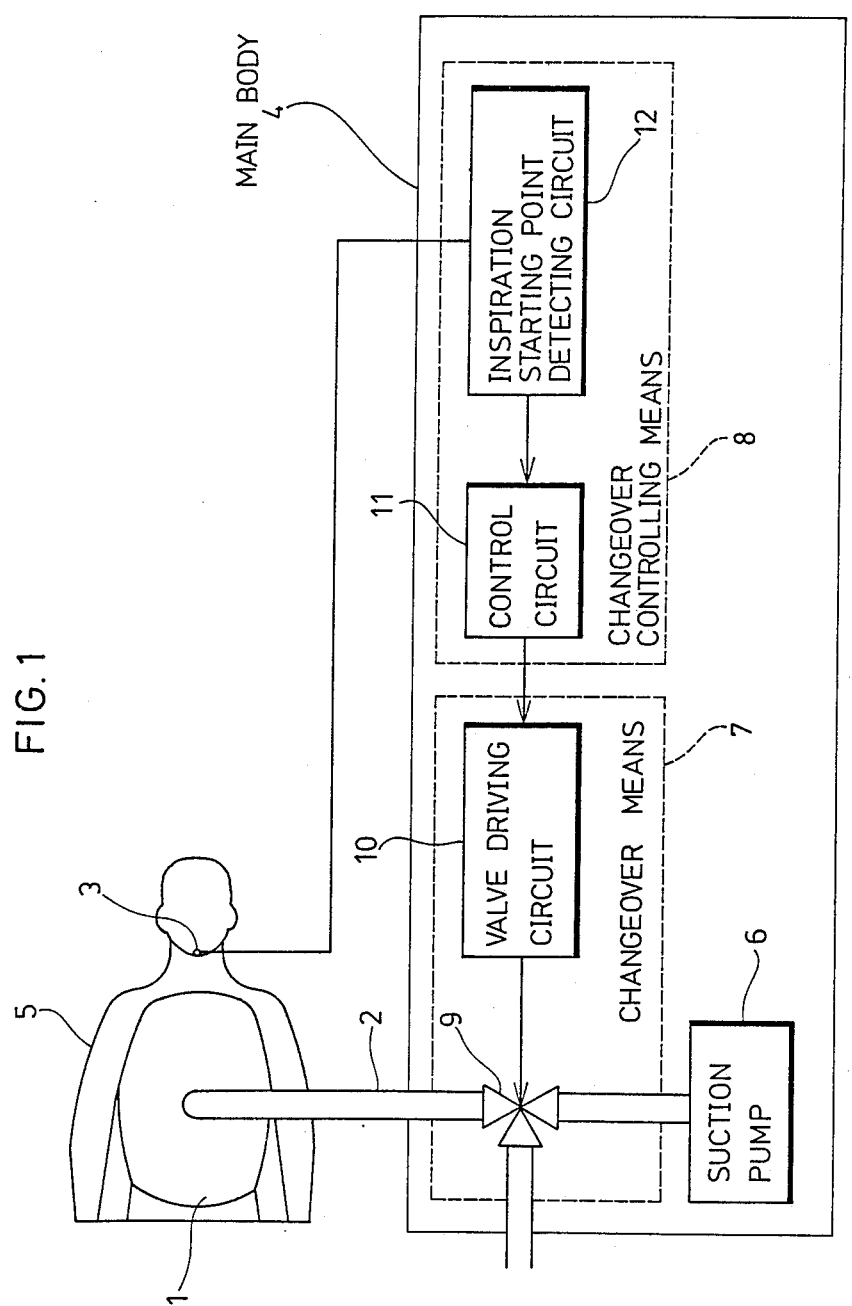
FIG. 1 is a schematic diagram of an external body ventilator in accordance with the principles of the present invention.

Referring now to the accompanying drawings, the preferred embodiment of the present invention will be described.

FIG. 1 is a schematic diagram of an external body ventilator, i.e. artificial breathing apparatus, in accordance with an embodiment of the present invention. In FIG 1, reference number 1 denotes a jacket; 2 denotes an air suction pipe; 3 denotes an acceleration pick-up; and 4 denotes a main body of this apparatus.

Jacket 1 comprises a portion of a rigid shell in the form of a tortoise shell and a belt-like portion. The portion of the rigid shell has a configuration for surrounding the chest of a patient 5, and the inside of the peripheral portion thereof is provided with packing constituted by an elastic member. The portion of the rigid shell is mounted on the chest of the patient via this elastic packing. The belt-like portion covers the rear surface of the patient 5, and the opposite end portions thereof reach the opposite side portions of the rigid shell mounted on the chest, and are retained by planar fasteners respectively provided thereon.

As the jaw movement detection means of the present invention, the acceleration pick-up 3 is installed on the jaw of patient 5, and produces as output, a signal representive of the acceleration of jaw movement.

One end of the suction pipe 2 is connected to a connection port provided in the rigid shell of the jacket 1, and is connected to the air-tight chamber which is formed when the jacket 1 is applied to the patient 5.

The main body 4 comprises a suction pump 6, a changeover means 7 and a changeover controlling means 8. The changeover means 7 includes a three-way valve 9 and a valve driving circuit 10 for driving the three-way valve 9. The three-way valve 9 has three connecting ports. The first connecting port is connected to the other end of the suction pipe 2, the second connecting port is open to the atmosphere, and the third connecting port is connected to the suction pump 6. The three-way valve 9 is adapted to effect a changeover between (i) connecting the suction pipe 2 to the suction pump 6, and (ii) releasing the air through the suction pipe 2 into the atmosphere, by means of the valve driving circuit 10.

The changeover controlling means 8 comprises a control circuit 11 and an inspiration starting point detection circuit 12. The inspiration starting point detection circuit 12 determines a change in the velocity involved in the movement of the patient's jaw which is detected by the acceleration pick-up 3. The signal produced from the acceleration pick-up 3 is provided to the inspiration starting point detection circuit 12. The inspiration starting point detection circuit 12 determines a change in the velocity (e.g. speed) involved in the movement of the jaw sensed by the acceleration pick-up 3, and detects the inspiration starting point from this change in jaw velocity.

Applicants have observed that the jaw moves upwardly during inspiration and downwardly during expiration, and using acceleration pick-up 3, signals indicating such jaw movement can be used in cooperation with the inspiration starting point detector circuit 12 to detect the inspiration starting point, from measurable changes in such signals. Therefore, during a point of time when the direction of the movement of the jaw shifts from the downward direction to the upward direction, this change of direction of jaw movement indicated by the signal can be used to set the inspiration starting point.

Referring to FIGS. 1 and 2, it is noted that the function of the control circuit 11 is to constantly monitor the interval between detected signals supplied from the inspiration starting point detection circuit 12, and also to determine whether this interval is within the predetermined time period $T_1$ or not as indicated in FIG. 2. When the control circuit 11 determines that this interval is within the time $T_1$, the control circuit 11 assumes that the patient 5 is performing voluntary breathing, and controls the valve driving circuit 10 in response to the timing of the detected signals. When the control circuit 11 determines that the interval has exceeded the time $T_1$, the control circuit assumes that the patient has suspended his or her voluntary breathing, and controls the valve driving circuit 10 at a predetermined timing.

The operation of the apparatus of the preferred embodiment so arranged will be described with reference to the timing chart shown in FIG. 2. First, the operator applies jacket 1 to the patient 5, and connects the suction pipe 2 to the connecting port provided in the jacket 1. At this time, an air-tight chamber is formed between the portion of the rigid shell of the jacket 1 and the chest of the patient 5. The operator applies the acceleration pick-up 3 to the jaw of the patient 5, and then the three-way valve 9 is set in such a manner as to release the air through the suction pipe 2 into the atmosphere. The operator then switches on the power source of the main body 4. The acceleration pick-up 3, applied to the jaw of the patient, produces signals corresponding to the movement of the patient's jaw during breathing movements.

Upon detecting the inspiration starting point from the output signal supplied from the acceleration pick-up 3, the inspiration starting point detection circuit 12 generates a detection signal which is provided to the control circuit 11 on each such occasion. When the control circuit determines that the interval of the detection signal supplied from the detection circuit 12 is within the time $T_1$, the control circuit 11 produces a signal to the valve driving circuit 10, for effecting connection of the suction pipe 2 to the suction pump 6. After a predetermined time $T_2$ (where $T_2$ is shorter than one cycle of voluntary breathing) from the detection signal, the control circuit 11 produces an output signal which is provided to the valve driving circuit 10 causing circuit 10 to release the air through the suction pipe 2 into the atmosphere.

The valve driving circuit 10 effects the changeover of the three-way valve 9 on the basis of the above signals, and the suction pipe 2 is connected to the suction pump 6 at each inspiration starting point of a cycle of voluntary breathing by the patient 5. The air in the air-tight chamber is released through the suction pipe 2 into the atmosphere after a lapse of the predetermined time $T_2$. Correspondingly, the air-tight chamber formed in the jacket 1 repeatedly and alternately assumes a predetermined negative-pressure and atmospheric pressure.

Meanwhile, when the control circuit 11 determines that the interval between the detection signals supplied from the inspiration starting point detection circuit 12 has exceeded the time $T_1$, the control circuit 11 provides to the valve driving circuit 10 a signal for connecting the suction pipe 2 to the suction pump 6. The control circuit 11 also provides to the valve driving circuit 10, a signal for releasing air from the air-tight chamber through the suction pipe 2 into the atmosphere after the predetermined time $T_2$. This release of air from the air-tight chamber, occurs after $T_2$ each time the control signal is produced from the control circuit 11. The valve driving circuit 10 effects the changeover of the three-way valve 9 on the basis of these signals, and the suction pipe is connected to the suction pump 6 at the intervals of the predetermined time $T_1$, and the air is released through the suction pipe 2 into the atmosphere after the predetermined time $T_2$ from that point of time. In response to such control operations, the air-tight chamber formed in the jacket 1 repeatedly and alternately assumes the negative-pressure and atmospheric pressure. The aforementioned times $T_1$ and $T_2$ are set in advance in the control circuit 11 and are variable.

In accordance with the above described embodiment, when the patient is breathing voluntarily, artificial respiration is effected by the apparatus in synchronism with the breathing of the patient, and, when the patient has ceased breathing voluntarily, artificial respiration is performed by the apparatus of the present invention at a predetermined timing as described hereinbefore. Furthermore, the changeover therebetween is carried out automatically.

In the above described embodiment, the timing of the voluntary breathing of the patient is obtained by detecting the inspiration starting point. However, this timing can be obtained by detecting the expiration starting point, or by detecting both inspiration and expiration starting points.

In addition, in the foregoing embodiment, an acceleration pick-up 3 is used as the jaw movement detecting means which produces a signal corresponding to the movement of the jaw of the patient during breathing movements. However, in an alternative embodiment, the jaw movement detection means can be realized, for example, by a displacement sensor. In this alternative embodiment, the displacement sensor is applied to the patient's jaw in such a manner as to produce an output signal corresponding to the distance traversed between two points, one of which is on the patient's jaw and the other being on the patient's throat. The signal produced from the displacement sensor, corresponds to the movement of the patient's jaw in a similar way as sensed by the above-described acceleration pick-up 3.

While the particular embodiments shown and described above have been proven to be useful in many applications involving the artificial respiratory arts, further modifications of the present invention herein disclosed will occur to persons skilled in the art to which the present invention pertains and all such modifications are deemed to be within the scope and spirit of the present invention defined by the appended claims.

What is claimed is:

1. Apparatus for effecting artificial respiration in synchronism with a patient's voluntary breathing, which comprises:
   a jacket having a rigid shell for surrounding the chest of a patient and forming an air-tight chamber between said chest and said rigid shell when said jacket is applied to said chest of said patient;
   a suction pump;
   a suction pipe in fluid communication with said air-tight chamber of said jacket;
   changeover means for effecting a changeover between releasing the air in said air-tight chamber through said suction pipe and into the atmosphere during exhalation and connecting said suction pipe to said suction pump during inhalation;
   an acceleration detection means installable on the jaw of said patient for producing a signal which directly corresponds to the movement of said jaw; and
   changeover controlling means for determining a timing of voluntary breathing by said patient on the basis of said signal produced by said acceleration detection means, and for controlling said changeover means on the basis of said timing, said changeover controlling means controlling said changeover means at a predetermined timing when the timing of said patient's breathing movement exceeds a predetermined time interval.

* * * * *